US00PP17132P2

(12) United States Plant Patent
Egger

(10) Patent No.: US PP17,132 P2
(45) Date of Patent: Oct. 3, 2006

(54) ***HEUCHERA* PLANT NAMED 'FANDANGO'**

(50) Latin Name: ***Heuchera* hybrid**
Varietal Denomination: Fandango

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 3 days.

(21) Appl. No.: 11/158,497

(22) Filed: Jun. 21, 2005

(51) Int. Cl.
*A01H 5/00* (2006.01)

(52) U.S. Cl. ..... Plt./263
(58) Field of Classification Search ..... Plt./263
See application file for complete search history.

*Primary Examiner*—Kent Bell
(74) *Attorney, Agent, or Firm*—Klarquist Sparkman, LLP

(57) ABSTRACT

A new and distinct hybrid of *Heuchera* plant characterized by well veiled, lightly ruffled, chocolate-colored foliage, warm pink flowers on short dark stalks, a mounding habit, and excellent vigor.

1 Drawing Sheet

Botanical denomination: *Heuchera* hybrid.
Variety designation: 'Fandango'.

The present invention relates to a new and distinct cultivar of *Heuchera* hybrid and given the cultivar name of 'Fandango'. *Heuchera* is in the family Saxifragaceae. *Heuchera* 'Fandango' originated from a cross between *Heuchera* 16-2 (an unpatented, proprietary plant) as the seed parent, and *Heuchera* 42-1 (an unpatented, proprietary plant) as the pollen parent. Given its ornamental foliage and flower form, it is probable that *Heuchera sanguinea, H. americana,* and *H. micrantha* are in its parentage.

This new *Heuchera* is distinguished by:

1. Leaf edges cut and lightly ruffled,
2. Leaves strongly silver veiled between reticulate veins,
3. Pink, wand type flowers on numerous flowering stems,
4. Mounding habit,
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

DETAILED PLANT DESCRIPTION

Figure 1:
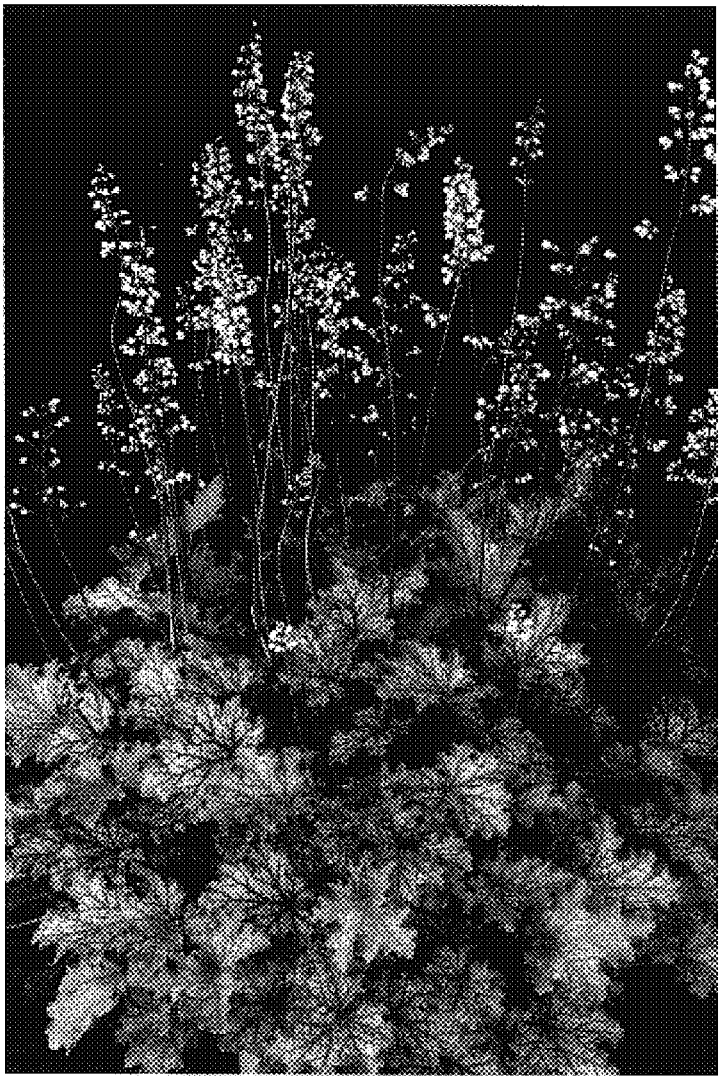
FIG. 1 shows a two-year-old plant of *Heuchera* 'Fandango' growing in a three gallon container in the shade house in May in Canby, Oreg.
Figure 2:
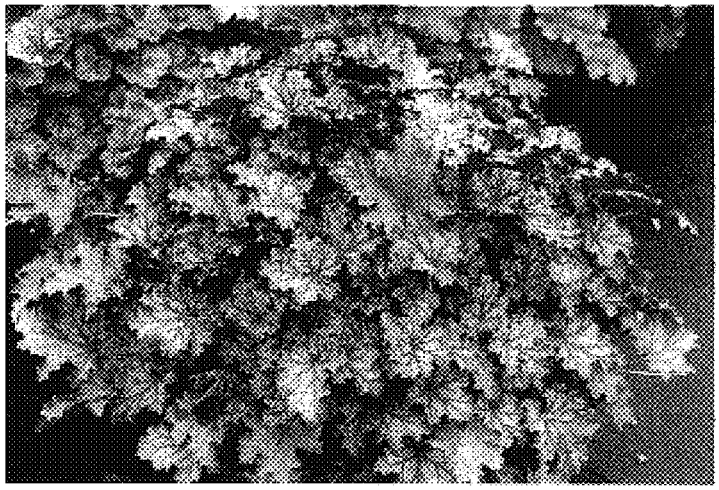
FIG. 2 shows the winter color of the foliage.

The following is a detailed description of the new *Heuchera* cultivar based on observations taken in May of a two-year-old specimen grown a three gallon container in an open air shade house with 50% shade cover and added irrigation in the summer months in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart.

Botanical classification: *Heuchera* hybrid.
Variety denomination: 'Fandango'.
Parentage: *Heuchera* 16-2×42-1 (both proprietary, unreleased plants).

Plant:
- *Form.*—Basal rosette, herbaceous perennial.
- *Hardiness.*—USDA Zone 4 to 9.
- *Size.*—22 cm tall from the ground to the top of the foliage and 50 cm wide.
- *Habit.*—Mounding.
- *Vigor.*—Excellent.
- *Roots.*—Fibrous, freely branching, fine, and white in color. Roots develop easily from cuttings.

Leaf:
- *Type.*—Simple.
- *Arrangement.*—Rosette.
- *Shape.*—Ovate.
- *Lobing/division.*—5 main lobes, each with one or two secondary lobes.
- *Venation.*—Palmate.
- *Margins.*—Deeply crenate and gently undulate giving a ruffled appearance, glandular.
- *Apex.*—Mucronulate.
- *Base.*—Cordate, lobes sometimes overlapping at the base.
- *Blade size.*—7.5 to 9.3 cm long and 6.5 to 8.2 cm wide.
- *Surface texture.*—Top surface is glabrous, bottom has very short glands along main veins.
- *Petiole description.*—9 to 15 cm long and 3 mm wide with the surface having very short glandular hairs, color is Greyed Red 178A.
- *Leaf color.*—Topside —In spring and fall leaf edges and veins are Brown 200A with a pinkish silver veil between Greyed White 156D and Red Purple 62D. Summer leaves lighten to olive green, between Brown 200A and Greyed Green 197A with darker edges and with a veil of Greyed Green 198B. In winter some leaves develop a reddish tone, Greyed Purple 184A. Bottom side —Between Greyed Purple 187A and 186A.

Inflorescence:

*Type.*—Thyrse, in a wand shape.

*Number of flowers.*—60 to 70 per thyrse.

*Number of thyrse in spring.*—70 in first flush.

*Peduncle.*—With 0 to 1 cauline leaf, 30 to 52 cm tall and 3 mm wide at the base, Greyed Purple 187B, very short glandular hairs.

*Pedicel.*—Variable in length, Greyed Purple 187B, very short glandular hairs.

*Bloom period.*—May and through summer in Canby, Oreg.

Flower bud:

*Size.*—2.5 mm wide and 4 mm long.

*Description.*—Glandular, ovoid.

*Color.*—Red 54A to 54C.

Flower:

*Type.*—Perfect, zygomorphic.

*Shape.*—Campanulate.

*Size.*—7 mm long and 5 mm wide.

*Petal count.*—5, inconspicuous.

*Petal color.*—Light pink, Red 54D on both sides.

*Petal shape.*—Spatulate with a clawed base, tips acute, margin entire.

*Petal size.*—2 mm long and 0.7 mm wide.

*Calyx.*—5 lobes, divided ⅓ way to the base, glandular, tips acute, margin entire.

*Calyx and flower size.*—7 mm long and 5 mm wide.

*Calyx and overall flower color.*—Pink on both sides, Red 54A at both ends and Red 54C in the middle. Lobe tips are Greyed Purple 187C.

*Stamen description.*—5 in number, filaments 3.5 mm long, White 155D, anthers sterile, no pollen produced, oval and about 0.5 mm long, Yellow Green 2D.

*Pistil description.*—5 mm long, White 155B except for ovary which is Yellow Green 2D, stigma is 2 parted.

*Fragrance.*—None.

*Lastingness.*—Each thyrse blooms for about 2 weeks on the plant.

Fruit:

*Type.*—Two-beaked ovoid capsule.

*Color.*—Brown 200D.

Seed:

*Shape.*—Linear.

*Size.*—2 mm long.

*Color.*—Black 202A.

Pest and disease tolerance: Excellent disease resistance to powdery mildew, the common problem of *Heuchera.* Susceptible to *Heuchera* rust and root weevils.

COMPARISON TO SIMILAR HEUCHERA

Compared to *Heuchera* 'Vesuvius' (U.S. Plant Pat. No. 13,215), this new variety has heavily veiled leaves with more lobes, and dark pink rather than dull red flowers.

Compared to *Heuchera* 'Autumn Haze' (U.S. Plant Pat. No. 12,160), *Heuchera* 'Fandango' has wand type flowers and darker leaves that are more lobed.

Compared to the seed parent *Heuchera* 16-2, the new variety has larger, more ruffled leaves, smaller flowers, and a larger plant size.

Compared to the pollen parent *Heuchera* 42-1, the new variety has larger showier flowers and heavy veiling rather than no leaf veiling.

I claim:

1. A new and distinct hybrid of *Heuchera* plant as herein illustrated and described.

* * * * *